(12) United States Patent
Goldman et al.

(10) Patent No.: US 9,289,759 B2
(45) Date of Patent: Mar. 22, 2016

(54) IRIDIUM CATALYST COMPLEXES AND C—H BOND ACTIVATED PRODUCTS THEREFROM

(75) Inventors: Alan Stuart Goldman, Highland Park, NJ (US); Robert Timothy Stibrany, Long Valley, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 508 days.

(21) Appl. No.: 13/611,089

(22) Filed: Sep. 12, 2012

(65) Prior Publication Data

US 2013/0245277 A1 Sep. 19, 2013

Related U.S. Application Data

(60) Provisional application No. 61/533,847, filed on Sep. 13, 2011.

(51) Int. Cl.
| | | |
|---|---|---|
| *B01J 31/18* | (2006.01) | |
| *C07F 15/00* | (2006.01) | |
| *C07C 5/333* | (2006.01) | |
| *C07C 5/52* | (2006.01) | |
| *C07C 17/20* | (2006.01) | |
| *B01J 23/46* | (2006.01) | |

(52) U.S. Cl.
CPC .............. *B01J 31/183* (2013.01); *B01J 23/468* (2013.01); *C07C 5/333* (2013.01); *C07C 5/52* (2013.01); *C07C 17/202* (2013.01); *C07F 15/004* (2013.01); *C07C 2531/22* (2013.01)

(58) Field of Classification Search
CPC ............................... B01J 31/183; C07F 15/004
See application file for complete search history.

(56) References Cited

U.S. PATENT DOCUMENTS

| | | |
|---|---|---|
| 5,755,999 A | 5/1998 | Shi et al. |
| 5,780,701 A | 7/1998 | Kaska et al. |
| 5,958,821 A | 9/1999 | Ishii et al. |
| 6,037,297 A | 3/2000 | Stibrany et al. |
| 6,689,928 B2 | 2/2004 | Stibrany et al. |
| 2002/0045790 A1 | 4/2002 | Stibrany et al. |
| 2005/0165180 A1 | 7/2005 | Nagy |
| 2005/0288464 A1 | 12/2005 | Kacker et al. |
| 2006/0115675 A1* | 6/2006 | Haga .................. C07F 15/0033 428/690 |
| 2006/0258043 A1 | 11/2006 | Bold et al. |
| 2007/0235728 A1 | 10/2007 | Kathirgamanathan et al. |
| 2010/0236984 A1 | 9/2010 | Brookhart et al. |

FOREIGN PATENT DOCUMENTS

| | | |
|---|---|---|
| WO | 2007008847 A2 | 1/2007 |
| WO | 2011/051749 A1 | 5/2011 |

OTHER PUBLICATIONS

Yutaka et al. "Syntheses and Properties of Emissive Iridium(III) Complexes with Tridentate Benzimidazole Derivatives" Inorganic Chemistry, 2005, vol. 44, pp. 4737-4746.*
Albrecht, Martin et al., "Platinum Group Organometallics Based on 'Pincer' Complexes: Sensors, Switches, and Catalysts", Angew. Chem. Int. Ed., 40: 3750-3781 (2001).
Belli, Jack et al., "Catalytic Alkane Dehydrogenation by IrC1H2(PPri3)2: Evidence for an Alkane Associative Mechanism", Organometallics, 15: 1532-1534 (1996).
Burk, Mark J. et al., "Selective Catalytic Dehydrogenation of Alkanes to Alkenes", J. Am. Chem. Soc., 109: 8025-8032 (1987).
Crabtree, Robert H. et al., "Alkane Dehydrogenation by Iridium Complexes", J. Am. Chem. Soc., 104: 107-113 (1982).
Fan, Hua-Jun et al., "Density functional studies of catalytic alkane dehydrogenation by an iridium pincer complex with and without a hydrogen acceptor", Journal of Molecular Catalysis A: Chemical, 189: 111-118 (2002).
Jensen, Craig M., "Iridium PCP pincer complexes: highly active and robust catalysts for novel homogeneous aliphatic dehydrogenations", Chem. Commun., 2443-2249 (1999).
Krogh-Jespersen, Karsten et al., "Computational and experimental studies of the mechanism of (PCP)Ir-catalyzed acceptorless dehydrogenation of alkanes", Journal of Molecular Catalysis A: Chemical, 189: 95-110 (2002).
Liu, Funchen et al., "Efficient thermochemical alkane dehydrogenation and isomerization catalyzed by an iridium pincer complex", Chem. Commun., 665-656 (1999).
Liu, Funchen et al., "Dehydrogenation of n-Alkanes Catalyzed by Iridium 'Pincer' Complexes: Regioselctive Formation of α-Olefins", J. Am. Chem. Soc., 121: 4086-4087 (1999).
Singleton, John T., "The uses of pincer complexes in organic synthesis", Tetrahedron, 59: 1837-1857 (2003).
Mas-Marz, E. et al., "Carbene Complexes of Rhodium and Iridum from Tripodal N-Heterocyclic Carbene Ligands: Synthesis and Catalytic Properties", Inorg. Chem., 43: 2213-2219 (2004).
Xu, X. et al., "Synthesis and structural characterization of copper (II) complexes of pincer ligands derived from benzimidazole", Journal of Coordination Chemistry, 60(21): 2297-2308 (2007).
Ishii, Yasutaka et al., "Alkane Oxidation with Molecular Oxygen Using a New Efficient Catalytic System: N-Hydroxyphthalimide (NHPI) Combined with Co(acac)n (n=2 or 3)", J. Org. Chem., 61: 4520-4526 (1996).
Lyons, James E., "Selective Low Temperature Hydroxylation of Isobutane by Molecular Oxygen Catalyzed by an Iron Perhaloporphyrin Complex", Catalysis Letters, 8: 45-52 (1991).
Murahashi, Shun-Ichi et al., "Aerobic Oxidations of Alkanes and Alkene4s in the Presence of Aldehydes catalysed by Copper Salts", J. Chem. Soc. Chem. Commun., 139-149 (1993).
Murahashi, Shun-Ichi et al., "Ruthenium-Catalyzed Cytochrome P-450 Type Oxidation of Alkanes with Alkyl Hydroperoxides", Tetrahedron Letters, 34(8): 1299-1302 (1993).

(Continued)

*Primary Examiner* — Joseph Kosack
(74) *Attorney, Agent, or Firm* — Patrick J. Hagan; Dann, Dorfman, Herrell and Skillman, P.C.

(57) ABSTRACT

Provided is a novel iridium catalyst complex which is useful in the dehydrogenation of alkanes. The iridium complex comprises the metal iridium atom complexed with a benzimidazolyl-containing ligand. The iridium atom can be coordinated with the nitrogen atoms in the benzimidazolyl-containing ligand to form an NCN pincer ligand complex. In another embodiment, the iridium catalyst is used, with or without a co-catalyst, in a dehydrogenation reaction converting alkanes to olefins. The reaction can be in a closed or open system, and can be run in a liquid or gaseous phase.

13 Claims, 1 Drawing Sheet

(56) References Cited

OTHER PUBLICATIONS

International Search Report/Written Opinion from related International Application No. PCT/US12/55150, filed Sep. 13, 2012.

Chianese, Anthony R. et al., "Iridium Complexes of CCC-Pincer N-Heterocyclic Carbene Ligands: Synthesis and Catalytic C—H Functionalization", Organometallics, 29: 3019-3026 (2010).

Crabtree, Robert H. et al., "Alkane Dehydrogenation by Iridum Complexes", J. Am. Chem. Soc., 104: 107-113 (1982).

Gayathri, V. et al., "Reactions of rhodium and iridium salts with multidentate N-heterocycles", Polyhedron, 16(7): 1169-1176 (1997).

Liu, Fuchen et al., "Dehydrogenation of n-Alkanes Catalyzed by Iridium "Pincer" Complexes: Regioselective Formation of Alpha-Olefins", J. Am. Chem. Soc., 121: 4086-4087 (1999).

Zhu, Keming et al., "Highly Effective Pincer-Ligated Iridium Catalysts for Alkane Dehydrogenation, DFT Calculations of Relevant Thermodynamic, Kinetic, and Spectroscopic Properties", JACS, 126(40): 13044-13053 (2004).

Extended European Search Report, dated Mar. 16, 2015, issued in corresponding European Patent Application 12838499.7.

* cited by examiner

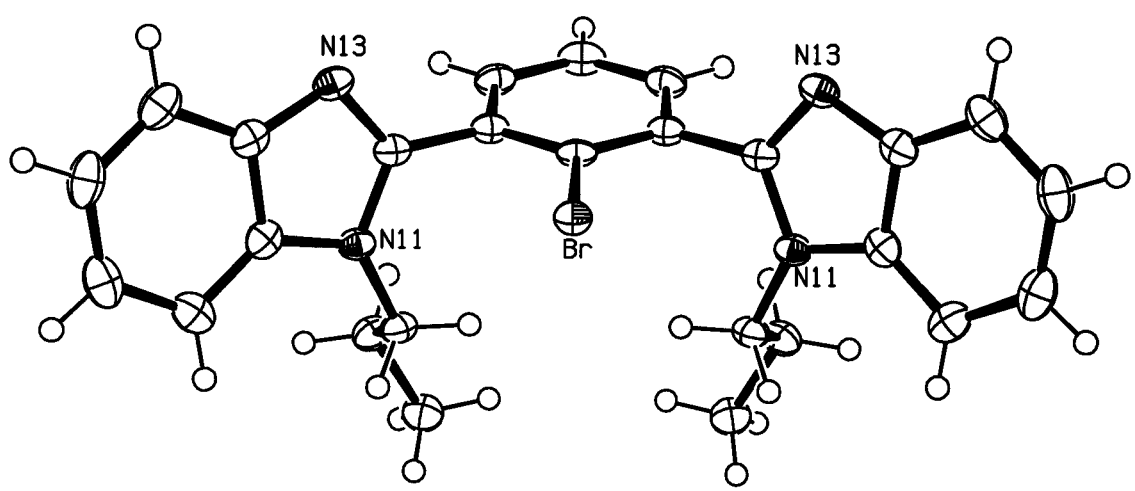

IRIDIUM CATALYST COMPLEXES AND C—H BOND ACTIVATED PRODUCTS THEREFROM

CROSS-REFERENCE TO RELATED APPLICATIONS

The present application claims the benefit of U.S. Provisional Patent Application No. 61/533,847, filed Sep. 13, 2011, the entire disclosure of which is incorporated by reference herein.

BACKGROUND OF THE INVENTION

1. Field of the Invention

Provided is the preparation and use of novel transition metal catalysts, which can be used to generate olefins from alkyl-containing molecules. More specifically, novel iridium metal catalysts with benzimidazolyl-containing ligands coordinated with the iridium are provided, which are useful for generating olefins from alkanes.

2. Description of the Related Art

Olefins can be generated by direct dehydrogenation with the removal of hydrogen gas or by the use of an acceptor such as ethylene to generate ethane. The chemical industry uses olefins as intermediates in a variety of processes. The largest chemical use is linear α-olefins used in the formation of polyolefins such as ethylene-1-octene copolymers. Also and most importantly, low carbon number olefins have the potential to be converted into higher carbon number molecules that would be suitable for fuels, particularly, diesel. Other products formed from olefins include surfactants, lubricants, and plasticizers.

Iridium complexes as catalysts are known. During the 1980s, it was discovered that certain iridium complexes are capable of catalytically dehydrogenating alkanes to alkenes under exceptionally mild thermal (i.e., less than 160° C.) or even photolytic conditions (see, e.g., *J. Am. Chem. Soc.* 104 (1982) 107; 109 (1987) 8025; *J. Chem. Soc., Chem. Commun.* (1985) 1829). For a more recent example, see *Organometallics* 15 (1996) 1532.

Pincer ligand complexes of rhodium and iridium as catalysts for the dehydrogenation of alkanes are receiving widespread attention. See, for example, F. Liu, E. Pak, B. Singh, C. M. Jensen and A. S. Goldman, "Dehydrogenation of n-Alkanes Catalyzed by Iridium "Pincer" Complexes: Regioselective Formation of alpha-olefins," *J. Am. Chem. Soc.* 121 (1999) 4086-4087; F. Liu and A. S. Goldman, "Efficient thermochemical alkane dehydrogenation and isomerization catalyzed by an iridium pincer complex," *Chem. Comm.* 1999, 655-656; and C. M. Jensen, "Iridium PCP pincer complexes: highly active and robust catalysts for novel homogenous aliphatic dehydrogenations," *Chem. Comm.* (1999) 2443-2449. The use of compounds such as $(PCP)MH_2$ $(PCP=C_6H_3(CH_2PBut_2)_2-2,6)$ (M=Rh, Ir) (1a, 1b) dehydrogenate various cycloalkanes to cycloalkenes at 200° C. with turnovers of 70-80 turnovers/hour. The reaction proceeds at 200° C. in neat solvent and without the use of a sacrificial hydrogen acceptor such as tert-butyl ethylene.

In addition, "pincer" complexes of platinum-group metals have been known since the late 1970s (see, e.g., *J. Chem. Soc., Dalton Trans.* (1976) 1020). Pincer complexes have a metal center and a pincer skeleton. The pincer skeleton is a tridentate ligand that generally coordinates with the meridional geometry. The use of pincer complexes in organic synthesis, including their use as low-temperature alkane dehydrogenation catalysts, was exploited during the 1990s and is the subject of two review articles (see *Angew. Chem. Int. Ed* 40 (2001) 3751 and Tetrahedron 59 (2003) 1837). See also U.S. Pat. No. 5,780,701. Jensen et al. (*Chem. Commun.* (1997) 461) used iridium pincer complexes to dehydrogenate ethylbenzene to styrene at 150 to 200° C. Recently, pincer complexes have been developed that dehydrogenate hydrocarbons at even lower temperatures. For some recent examples, see *J. Mol. Catal. A* 189 (2002) 95, 111 and *Chem. Commun.* (1999) 2443.

Despite the extensive research into new catalysts and methods for producing valuable olefin compounds, the search for catalysts which are more stable, as well as more thermally and chemically robust continues. Such catalysts would make the preparation of valuable olefin compounds more economic and efficient.

SUMMARY OF THE INVENTION

Provided is a novel iridium catalyst complex which is useful in the dehydrogenation of alkanes. The iridium complex comprises the metal iridium atom complexed with a benzimidazolyl-containing ligand. The iridium atom can be coordinated with the nitrogen atoms in the benzimidazolyl-containing ligand to form an NCN pincer ligand complex.

In another embodiment, the iridium catalyst is used, with or without a co-catalyst, in a dehydrogenation reaction converting alkanes to olefins. The reaction can be in a closed or open system, and can be run in a liquid or gaseous phase.

Among other factors, it has been discovered that when iridium complexes with a benzimidazolyl-containing ligand, a more stable and active catalyst is obtained. The catalyst demonstrates improved activity and lifetime when used in a dehydrogenation reaction as compared to conventional catalysts.

BRIEF DESCRIPTION OF THE FIGURE OF THE DRAWING

The FIGURE shows one embodiment of the crystal structure of 2,2'-(2-bromo-1,3-phenylene)bis(1-propylbenzimidazol-2-yl).

DETAILED DESCRIPTION OF THE INVENTION

Provided is a novel metal complex which, when used with or without an activating cocatalyst, provides a novel catalyst composition. Also provided is an iridium catalyst complex useful in the dehydrogenation of alkanes comprising iridium complexed with a benzimidazolyl-containing ligand. Also provided is a novel dehydrogenation method which utilizes the catalyst composition.

Iridium complexed with a benzimidazolyl-containing ligand is unique. It has been found that changing the metal within the same group (column) of the periodic table, for example to rhodium, changes the bond strength which then adversely affects the ability of the catalyst to, e.g., effect the dehydrogenation of an alkane. Changing the metal to another group, for example to osmium or platinum, alters the electronic configuration of the metal which would potentially require altering the ligand to accommodate greater or fewer valence electrons which would of course alter the catalytic activity. Thus, the specific Ir(NCN) catalyst as described herein is unique.

The iridium catalyst complex is of the formula $LMX(X')_n$ where n=0, 1 or 2, X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl, olefins including diolefins, and any other moiety or which can be eliminated from the metal center to generate a catalytically active LM fragment. M is iridium. L is a nitrogen-containing ligand having two or more nitrogen atoms. In a preferred embodiment L has the formula:

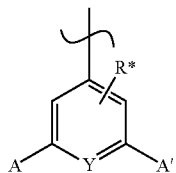

wherein A and A' are independently selected from the group consisting of:

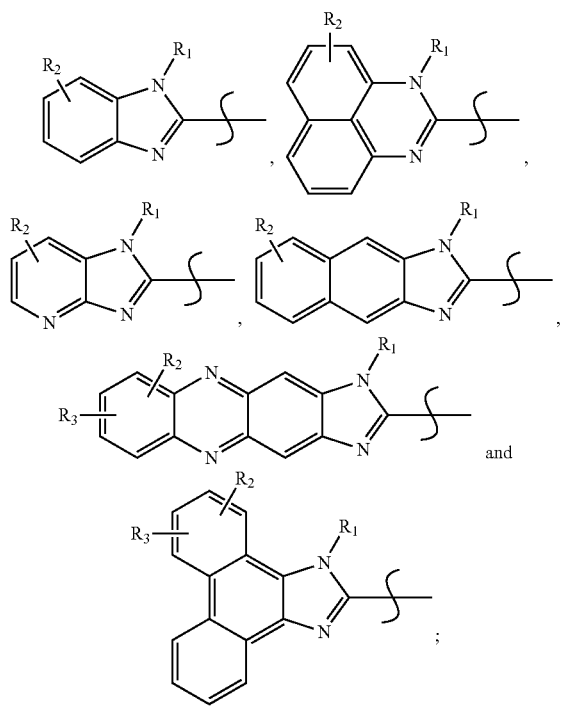

$R_1$, $R_2$, $R_3$ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—OR$_4$, wherein R$_4$ is hydrogen, an optionally substituted acyl group, e.g. acetyl or trifluoroacetyl, or an optionally substituted alkylsulfonyl group, e.g. methylsulfonyl or trifluoromethylsulfonyl and other leaving group; and p=0, 1 or 2.

The nitrogen-containing ligands can be synthesized using techniques well known to those skilled in the art. See, for example, U.S. Pat. Nos. 6,037,297 and 6,689,928 and U.S. patent application Ser. No. 13/611,072 (RU 2011-073, "Process for the Oxidation of Hydrocarbons with the Use of Iridium Metal Catalyst Complexes" of Alan Stuart Goldman and Robert Timothy Stibrany, filed concurrently with the subject application), the foregoing documents being specifically incorporated herein by reference in their entirety. In general, the novel iridium catalyst complex can be synthesized by reacting complexing Ir salts with the ligands. This can be accomplished, for example, by dissolving the Ir salt in a solvent, and then adding the ligand. The mixture is then refluxed and cooled. The Figure depicts such a ligand compound.

The invention also provides for the composition having the formula LMX(X')$_n$, as defined above, and an activating cocatalyst. The activating cocatalyst can be selected from the group consisting of alkylalumoxanes, aluminum alkyls, aluminum halides, alkyl aluminum halides, Lewis acids such as tris(pentafluorophenyl)borane, alkylating agents, hydrides such as lithium hydride, reducing agents such as Na/K amalgam, and mixtures thereof. The preferred ratio of metal complex to activating cocatalyst is from $1:10^{-2}$ to $1:10^6$.

The composition described above may also be supported. The support material maybe a porous material, which includes, but is not limited to, inorganic oxides, zeolites, and inorganic chlorides. The support may also be resinous materials such as polystyrene, polyolefin, and other polymeric materials. These catalysts maybe physiosorbed on the support or chemically bonded to the support.

In the catalyst composition, the iridium can be coordinated with the nitrogen atoms in the benzimidazolyl-containing ligand to form a NCN pincer ligand complex. The NCN ligand derived from the benzimidazolyl-containing subunit is unique as compared to other NCN ligands or to the related PCP ligand group. As an example of improved activity/lifetime, Ir(PCP) catalysts deactivate after about 100 turnovers while the Ir(NCN) based on benzimidazolyl-containing ligands lasts essentially indefinitely. Also, Ir(PCP) reacts with nitrogen while Ir(NCN) experiments are commonly run under $N_2$ which narrows the applicability of PCP-based catalysts.

The novel composition of the invention can also be used in conjunction with a cocatalyst to dehydrogenate alkanes in order to provide olefins for subsequent reaction.

The catalyst is quite useful in dehydrogenating alkanes to olefins. The alkane starting materials can include straight and branched-chain compounds having from about 1-20 carbon atoms, such as methane, ethane, propane, n-butane, isobutane, n-pentane, n-hexane, 2-methylpentane, 3-methylpentane, heptane, 2-methylheptane, 3-methylheptane and the like. In one embodiment, the alkane has from 4-20 carbons. In another embodiment, the alkane is a $C_{12}$ alkane or higher.

The alkane reactant can also be a cycloalkane, where the term "cycloalkane" as used herein should be understood to include macrocyclic cycloalkanes having a carbon ring of 8 or more and up to 25 members and simple cycloalkanes having a carbon ring of less than 8 members but greater than 4 members e.g., cyclopentane, cyclohexane. Typically, the cycloalkane is a C5 to C20 membered ring.

Suitable cycloalkanes for use in the process described herein include, for example, cyclopentane, cyclohexane, cycloheptane, cyclooctane, cyclononane, cyclodecane, cycloundecane, cyclododecane, cyclotridecane, cyclotetradecane, cyclopentadecane, cyclohexadecane, cyclooctadecane, cyclononadecane, cycloicosane, cyclodocosane or cyclotetracosane.

These alkane compounds, if desired, may be substituted with various moieties, although care should be taken to exclude substituents which will adversely affect the activity of the catalyst.

One issue with "non-oxidative" or "acceptor-less" alkane dehydrogenation is the hydrogen that is co-formed during the process. When chemical reactions are in equilibrium, products must be removed in order for the chemical reaction to proceed further to the right. Also, a build-up of hydrogen can poison a catalyst by preferentially binding to the metal center. Thus, in one embodiment of the present process, alkane dehydrogenation is run with a ($C_{12}$) alkane that boils at high temperature in an open flask. In this way the hydrogen formed is swept out of the reaction medium and the reaction is allowed to proceed.

In "oxidative dehydrogenation", more common in the literature, the dehydrogenation reaction is coupled with oxygen to form water at high temperature. This chemistry is usually run in the gas phase with a heterogeneous catalyst.

In another embodiment, the dehydrogenation process is run in the presence of a hydrogen acceptor, usually a less valuable olefin, where the hydrogen is consumed in a secondary hydrogenation reaction with the acceptor olefin. This is common in a closed system, for example where a low boiling alkane is the reactant. Generally, since an elevated temperature is required for the endothermic dehydrogenation reaction, one uses a pressure reactor with a volatile alkane, and in this case an acceptor is required for the reaction to run to any significant conversion.

In general, the dehydrogenation reaction can be run under conventional dehydrogenation reaction conditions. The Ir catalyst of the present invention does not, however, require high temperatures or pressures. Therefore, the reaction can be run at temperatures less than 300° C., even less than 200° C., and in one embodiment, at room temperature up to about 160° C. The pressure is adjusted accordingly.

The following examples are provided to further illustrate the present invention, but are not meant to be limiting.

Example 1

Preparation of 2,2'-(1,3-phenylene)bis(1-propylbenzimidazol-2-yl)

In a 50 mL Erlenmeyer flask, 450 mg of 2,2'-(2-bromo-1,3-phenylene)bis(1-hydrobenzimidazol-2-yl) (1.45 mmol) was added. Then 15 mL of N,N-dimethylformamide was added followed by the addition of 300 µL of 1-iodopropane (3.13 mmol). Then 800 mg of powdered NaOH was added to the mixture. After 0.5 hours the mixture had turned light brown. The flask was stoppered and left to stir overnight at room temperature. The reaction was then quenched with water. The reaction mixture was then extracted with about 40 mL of ethyl acetate and 60 mL of water. The pale-brown organic phase was separated and placed in a beaker to evaporate. After evaporation of the volatiles, a pale-brown solid was obtained. $C_{26}H_{25}N_4$, fw=393.50. Mp: 168° C. (sft) 195° C. (melt). $^1$H NMR (300 MHz, $CDCl_3$): δ 7.81 (d, J=6.9 Hz, 2H), 7.65 (d, J=6.9 Hz, 2H), 7.58 (m, 1H), 7.31 (m, 6H), 3.99 (br m, 4H), 1.71 (q, J=6.4 Hz, 4H), J=6.4 Hz, 6H). $^{13}$C NMR (100 MHz, $CDCl_3$): δ 151.9, 145.1, 143.1, 134.8, 134.1, 134.0, 123.3, 122.7, 120.5, 110.6, 46.6, 23.1, 11.5. $R_f$=0.47 (ethyl acetate/silica). X-ray: a=25.261(7) Å, b=10.469(3) Å, c=8.527(2) Å, α=90°, β=90°, γ=90°, V=2255.0(10).

Example 2

Preparation of 2-chloro-5-tert-butyl-1,3-dimethylbenzene

In a 500 mL round bottom flask 4.50 g of 2-bromo-5-tert-butyl-1,3-dimethylbenzene (18.6 mmol) and 9.50 g of $NiCl_2.6H_2O$ (40.0 mmol) were added. Then 30 mL of N,N-dimethylformamide was added to the flask, giving a blue-green solution. The flask was fitted with a condenser and was left to reflux with stirring. After 0.5 hours the solution was dark blue. After refluxing for 5 days the mixture was cooled to rt and then diluted with 25 mL of 2 M HCl. The aqueous phase was extracted with 40 mL of ethyl acetate. The volatiles were removed from the extract by evaporation to give a white solid. (91% conversion to the title product) All of the solids were dissolved in 25 mL of N,N-dimethylformamide and the solution was placed in a 125 mL round bottom flask. Then 5.1 g of $NiCl_2.6H_2O$ (21.5 mmol) was added to the flask. The flask was fitted with a condenser and was left to reflux with stirring. After 0.5 hours the solution was dark blue. After refluxing for 5 days the mixture was cooled to rt and then diluted with 25 mL of 2 M HCl. The aqueous phase was extracted with 40 mL of ethyl acetate. The volatiles were removed from the extract by evaporation to give a white solid. $C_{12}H_{17}Cl$, fw=196.72. Yield 3.51 g, 95.6%. Mp: 39° C. (melt). $^1$H NMR (300 MHz, $CDCl_3$): δ 7.01(s, 2H), 2.30 (s, 6H), 1.22 (s, $R_f$=0.69 (cyclohexane/silica).

Example 3

Preparation of 2-chloro-5-tert-butyl-isophthalic acid

To a 250 mL round bottom flask 4.38 g of 2-chloro-5-tert-butyl-1,3-dimethylbenzene (22.3 mmol) was added. Then 40 mL of 1:1 v/v t-butanol/water was added to the flask. Then 8.00 g of $KMnO_4$ (50.6 mmol) was added and the mixture was refluxed for 1 hour and cooled to rt. An additional 8.00 g of $KMnO_4$ (50.6 mmol) was added and the mixture was refluxed for 4 days. The reaction mixture was then filtered hot and washed with an additional 10 mL of water. The filtrate was reduced in volume by about half by evaporation. The filtrate was then made acidic with conc. HCl. The mixture was then cooled in an ice/water bath for 0.5 hours. The precipitate was collected by filtration and was washed with 20 mL of water. The white solid was allowed to air dry. $C_{12}H_{13}ClO_4$, fw=256.68. Yield 5.38 g, 94.1%. Mp: 250° C. (soften) 264° C. (melt). $^1$H NMR (300 MHz, $CD_3COCD_3$): δ 7.90(s, 2H), 1.37 (s, 9H).

Example 4

Preparation of 3,4-dimethyl-1,2-phenylene diamine

To a 125 mL round bottom flask 2.20 g of 2,3-dimethyl-6-nitro-aniline (13.2 mmol) was added. Then 15 mL of ethanol was added to the flask followed by the addition of 4 mL of 20 wt % NaOH in water. Then 2.0 g of zinc dust was added to the flask. The flask was fitted with a condenser and was left to reflux with stirring. After about 0.5 hours the mixture became very pale-brown. After refluxing for 18 hours the mixture was filtered hot to give a pale filtrate which quickly became dark red. $C_8H_{12}N_2$, fw=136.19. Yield 1.78 g, 98.7%. Mp: 60° C. (melt). $^1$H NMR (300 MHz, $CDCl_3$): δ 6.54(s, 2H), 3.46 (br s, 2H), 3.21 (br s, 2H), 2.22 (s, 3H), 2.11 (s, 3H). $R_f$=0.68 (ethyl acetate/silica).

Example 5

Preparation of 2,2'-(5-tert-butyl-2-chloro-1,3-phenylene)bis(1-hydro-4,5-dimethylbenzimidazol-2-yl)

In a 125 mL round bottom flask 0.6128 g of 2-chloro-5-tert-butyl-isophthalic acid (2.40 mmol) and 0.650 g of 3,4-dimethyl-1,2-phenylenediamine (4.77 mmol) were added.

Then 10 mL of polyphosphoric acid was added to the flask. The flask was fitted with a condenser and heated to 190-200° C. with stirring. After 2 days the mixture was cooled to about 90° C. and then made basic (pH>9) with concentrated ammonium hydroxide. The mixture was diluted with 50 mL of water. The solids were collected by filtration, washed with water, and air dried. The solids were then placed in a 125 mL round bottom flask containing 2 g of activated carbon. Then 35 mL of ethanol were added to the flask. The flask was fitted with a condenser and was left to reflux with stirring. After refluxing for 10 days the mixture was cooled to it and then filtered. The solids were washed with an additional 10 mL of ethyl acetate. The clear filtrate was evaporated to give a pale-brown crystalline solid. $C_{28}H_{29}ClN_4$, fw=457.01. Yield 405 mg, 37.0%. Mp: 217° C. (soften) 265° C. (melt). $^1$H NMR (300 MHz, CDCl$_3$): δ 7.83(s, 2H), 7.34 (d, J=8.4 Hz, 2H), 7.09 (d, J=7.4 Hz, 2H), 2.51 (s, 6H), 2.38 (s, 6H), 1.39 (s, 9H). $R_f$=0.11 (ethyl acetate/silica).

Example 6

Preparation of 2,2'-(5-tert-butyl-2-chloro-1,3-phenylene)bis(1-propyl-4,5-dimethylbenzimidazol-2-yl)

In a 25 mL round bottom flask, 800 mg of 2,2'-(5-tert-butyl-2-chloro-1,3-phenylene)bis(1-hydro-4,5-dimethylbenzimidazol-2-yl) (1.75 mmol) was added. Then 6 mL of dimethyl sulfoxide was added slowly giving a pale yellow solution. Then 500 mg of NaH (95%) was slowly added and was allowed to stir an additional 15 min. Then 360 μL of 1-iodopropane (3.69 mmol) was added dropwise. The flask was sealed and the mixture was allowed to stir at room temperature. After 2 days the mixture was quenched with water. The reaction mixture was then extracted with about 40 mL of ethyl acetate and 40 mL of water. The organic phase was separated and reduced in volume to ca. 4 mL. The brown liquid was chromatographed on silica with ethyl acetate. The first pale yellow band was collected and taken to dryness to give a pale-yellow solid. $C_{34}H_{41}ClN_4$, fw=541.17. Yield 373 mg, 46.6%. Mp: 221° C. (soften) 254° C. (melt). $^1$H NMR (300 MHz, CDCl$_3$): δ 7.66(s, 2H), 7.18 (d, J=12.8 Hz, 2H), 7.15 (d, J=12.8 Hz, 2H), 4.07 (br m, 4H), 2.64 (s, 6H), 2.41 (s, 6H), 1.72 (q, J=7.1 Hz, 4H), 1.34 (s, 9H), 0.76 (t, J=7.1 Hz, 6H). $R_f$=0.81 (ethyl acetate/silica).

Example 7

Preparation of Ir[(κ$^3$N,C,N) 2,2'-(5-tert-butyl-1,3-phenylene)bis(1-propyl-4,5-dimethylbenzimidazol-2-yl)]dichloride In an argon glove box 60 mg of 2,2'-(5-tert-butyl-2-chloro-1,3-phenylene)bis(1-propyl-4,5-dimethylbenzimidazol-2-yl) (0.13 mmol) was placed in a 50 mL round bottom flask. This was followed by the addition of 37 mg of $Ir_2(COD)_2Cl_2$ (0.055 mmol) and 10.0 mL of acetonitrile. The flask was sealed with a septa. The flask contained a yellow-orange solution. After stirring at room temperature for one hour the mixture became orange. After stirring at room temperature for 38 hours, the volatiles were removed under vacuum to give a yellow glass. Acetone was added to the slurry and a steel blue solution was obtained. All of the volatiles were removed under vacuum to give a steel blue glass. $C_{34}H_{41}Cl_2IrN_4$, fw=768.84. IR(KBr pellet, cm$^{-1}$) 2963 s, 2933 s, 2875 m, 2831 w, 1466 s, 1382 m, 1327 w, 1298 w, 1146 w, 896 w, 789 m, 611 w, 494 w.

Example 8

Preparation of Ir[(κ$^3$N,C,N) 2,2'-(5-tert-butyl-1,3-phenylene)bis(1-propyl-4,5-dimethylbenzimidazol-2-yl)]ethylene In an Ar glovebox 10 mg of Ir[(κ$^3$N,C,N) 2,2'-(5-tert-butyl-1,3-phenylene)bis(1-propyl-4,5-dimethylbenzimidazol-2-yl)]dichloride was placed in a 125 mL round bottom flask. Then about 7 mL of benzene was added to give a yellow solution. Then 30 mg of Na/K alloy was added to the flask. The flask was sealed with a septa and taken to an ethylene line where the flask was flushed with ethylene and then left under a positive pressure of 5 prig of ethylene. The yellow-orange mixture was left to stir. After stirring for 18 hours, the volatiles were removed under vacuum to give an orange solid. $^1$H NMR (400 MHz, CDCl$_3$): δ 7.69(s, 2H), 7.14 (m, 2H), 7.08 (m, 2H), 4.69 (br m, 4H), 2.80 (s, 6H), 2.33 (s, 6H), 2.21 (s, 4H), 1.59 (m, 4H), 1.41 (s, 9H), 0.64 (m, 6H).

Example 9

Transfer Dehydrogenation

In an Ar glovebox 2.6 mg of [Ir[(κ$^3$N,C,N) 2,2'-(1,3-phenylene)bis(1-propylbenzimidazol-2-yl)]hydridobromide]$_2$ was placed in a 35 mL glass pressure reactor. Then 5.0 mL of toluene was added to give a brown solution with some suspended solid. Then 2.0 mL of 1-octene was added to the reactor. The reactor was sealed and was immersed in an oil bath at 110° C. and was left to stir for 95 h. GC analysis; 0.41% octane, 1.2% internal octene isomers, 0.45% dienes, 0.23% trienes, 0.47% dimers.

Example 10

Acceptorless Dehydrogenation

In an Ar glovebox 4.0 mg of [Ir[(κ$^3$N,C,N) 2,2'-(1,3-phenylene)bis(1-propylbenzimidazol-2-yl)]hydridobromide]$_2$ was placed in a flow through dehydrogenation apparatus. Then 6.0 mL of n-dodecane was added to give a very pale-brown solution with suspended solid. The apparatus was sealed and taken to an Ar Schlenk line. There a flow through rate of ca. 5 mL/min. was established. The condenser was connected and the reservoir was immersed in a sand bath and a gentle reflux was established. The dehydrogenation was run for 164 hrs. GC analysis; 0.003% 1-dodecene, 0.012% internal dodecene isomers, 0.015% dienes.

Various modifications and alterations of this invention will become apparent to those skilled in the art without departing from the scope and spirit of the invention. Other objects and advantages will become apparent to those skilled in the art from a review of the preceding description.

A number of patent documents and non-patent documents are cited in the foregoing specification in order to describe the state of the art to which this invention pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All iridium catalyst complexes and methods of use thereof that embody the present invention can, in alternate embodiments, be more specifically defined by any of the transitional terms "comprising", "consisting essentially of" and "consisting of".

That which is claimed is:

1. An iridium catalyst complex of the formula $LMX(X')_n$, where n =0, 1 or 2;
   X and X' are moieties which can be eliminated from the metal center to generate a catalytically active LM fragment;
   M is iridium; and
   L is the ligand 2,2'-(1,3-phenylene) bis (1-propylbenzimidazol 2 yl).

2. A catalyst composition comprising the iridium catalyst complex of claim 1 and a co-catalyst.

3. A method of dehydrogenating alkanes which comprises contacting an alkane under dehydrogenation conditions in the presence of an iridium catalyst complex of the formula $LMX(X')_n$, where n =0, 1 or 2;
   X and X' are moieties which can be eliminated from the metal center to generate a catalytically active LM fragment;
   M is iridium; and
   L is a ligand having the formula:

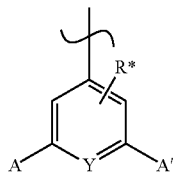

wherein A and A' are independently selected from the group consisting of:

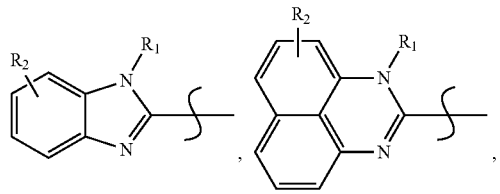

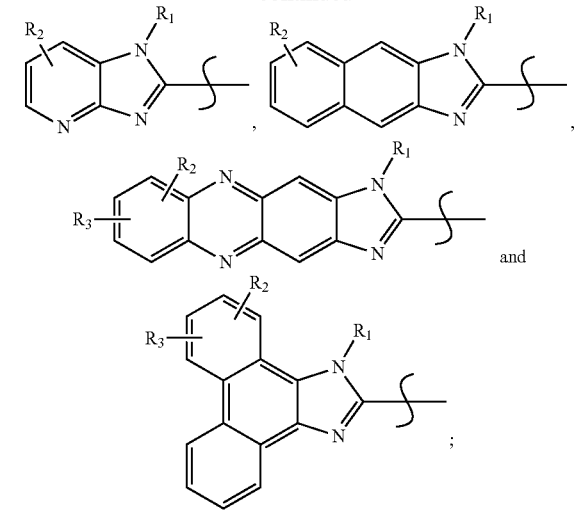

where $R_1$, $R_2$, $R_3$, and R* are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl and $C_7$ through $C_{17}$ aralkyl olefins;

and Y is selected from the group consisting of C—H, C—Cl, C—Br, C—I, N, P, C—$OR_4$ wherein $R_4$ is hydrogen, an optionally substituted acyl group, an optionally substituted alkylsulfonyl group or other leaving group; and p=0,1 or 2.

4. A method of dehydrogenating alkanes which comprises contacting an alkane under dehydrogenation conditions in the presence of the catalyst of claim 1.

5. The method of claim 3, wherein the reaction is run with a high boiling alkane having a boiling point of at least 200° C., in an open reactor.

6. The method of claim 5, wherein the alkane is a $C_{12}$ or higher alkane.

7. The method of claim 3, wherein the dehydrogenation reaction is run in the presence of oxygen.

8. The method of claim 3, wherein the reaction is run in a closed system.

9. The method of claim 8, wherein the reaction is run with an alkane which is lower than a $C_{12}$ alkane.

10. The method of claim 3, wherein the alkane is a $C_4$ - $C_{20}$ alkane.

11. The method of claim 3, wherein an olefin product is recovered.

12. The method of claim 7, wherein the contacting is conducted in the gaseous phase.

13. The method of claim 4, wherein a co-catalyst is used for the contacting.

* * * * *